US 9,028,446 B2

(12) United States Patent
Nemoto et al.

(10) Patent No.: US 9,028,446 B2
(45) Date of Patent: May 12, 2015

(54) CHEMICAL LIQUID INJECTION SYSTEM

(75) Inventors: Shigeru Nemoto, Tokyo (JP); Nobuhisa Tano, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 76 days.

(21) Appl. No.: 13/169,497

(22) Filed: Jun. 27, 2011

(65) Prior Publication Data

US 2011/0284577 A1    Nov. 24, 2011

Related U.S. Application Data

(63) Continuation of application No. 10/598,536, filed as application No. PCT/JP2005/003498 on Mar. 2, 2005, now Pat. No. 7,967,778.

(30) Foreign Application Priority Data

Mar. 3, 2004    (JP) .................................. 2004-059034

(51) Int. Cl.
  *A61M 1/00*    (2006.01)
  *A61M 5/145*   (2006.01)
  A61M 5/00     (2006.01)
  A61M 5/14     (2006.01)

(52) U.S. Cl.
  CPC ........... *A61M 5/14546* (2013.01); *A61M 5/007* (2013.01); *A61M 5/1408* (2013.01); *A61M 5/1456* (2013.01); *A61M 2205/505* (2013.01); *A61M 2205/581* (2013.01); *A61M 2205/583* (2013.01); *A61M 2205/6018* (2013.01); *A61M 2205/6054* (2013.01)

(58) Field of Classification Search
  USPC .............. 604/151, 152, 153, 65, 67, 131, 189
  See application file for complete search history.

(56) References Cited

U.S. PATENT DOCUMENTS

| 4,854,324 A |   | 8/1989  | Hirschman et al. |
|-------------|---|---------|------------------|
| 5,383,858 A |   | 1/1995  | Reilly et al.    |
| 5,573,515 A | * | 11/1996 | Wilson et al. .................. 604/236 |

(Continued)

FOREIGN PATENT DOCUMENTS

| JP | H06-154322  | 3/1994  |
|----|-------------|---------|
| JP | A-H06-277283 | 10/1994 |

(Continued)

OTHER PUBLICATIONS

Office Action mailed Oct. 26, 2011 in Corresponding Japanese Application No. 2006-510688.

(Continued)

*Primary Examiner* — Aarti B Berdichevsky
*Assistant Examiner* — Laura Schell
(74) *Attorney, Agent, or Firm* — Knobbe Martens Olson & Bear LLP

(57) ABSTRACT

RFID chip (214) having various types of data is mounted on liquid syringe (200). Chemical liquid injector (100) obtains the various types of data from RFID chip (214) to perform a predetermined operation in accordance with at least some of the various types of data. For, example, a variable pattern for liquid can be recorded on RFID chip (214) of liquid syringe (200) to allow chemical liquid injector (100) to inject the liquid in accordance with the predetermined variable pattern. Thus, a large amount of data can be easily input to the chemical liquid injector to perform the various operations.

19 Claims, 8 Drawing Sheets

(56) References Cited

U.S. PATENT DOCUMENTS

| | | |
|---|---|---|
| 5,653,938 A | 8/1997 | Faries, Jr. et al. |
| 6,254,572 B1 * | 7/2001 | Knipfer et al. ............... 604/151 |
| 6,743,202 B2 | 6/2004 | Hirschman et al. |
| 2001/0034506 A1 | 10/2001 | Hirschman et al. |
| 2002/0038392 A1 | 3/2002 | De La Huerga |
| 2003/0074223 A1 | 4/2003 | Hickle et al. |
| 2004/0073177 A1 | 4/2004 | Hickle |
| 2005/0029277 A1 * | 2/2005 | Tachibana ..................... 221/9 |
| 2005/0049556 A1 * | 3/2005 | Tanaka ......................... 604/152 |

FOREIGN PATENT DOCUMENTS

| | | |
|---|---|---|
| JP | A-2011-505104 | 4/2001 |
| JP | 2002-518108 A | 6/2002 |
| JP | A-2002-248167 | 9/2002 |
| JP | A-2003-070911 | 3/2003 |
| JP | 2003-250343 A | 10/2003 |
| JP | A-2004-501737 | 1/2004 |
| WO | WO 98/22168 | 5/1998 |
| WO | WO 02/04049 A1 | 1/2002 |
| WO | WO 02/20073 A2 | 3/2002 |
| WO | WO 02/051475 A1 | 7/2002 |
| WO | 03/011377 A1 | 2/2003 |
| WO | 03-024385 A1 | 3/2003 |
| WO | 03/026558 A2 | 4/2003 |
| WO | WO 03/097156 A1 | 11/2003 |
| WO | WO 03/105930 A2 | 12/2003 |

OTHER PUBLICATIONS

Office Action issued in Japanese Patent Application No. 2011-092107, mailed on Sep. 18, 2012.
Office Action issued on Mar. 19, 2013 for Japanese Patent Application No. JP2011-282390.
Office Action issued on Mar. 19, 2013 for Japanese Patent Application No. JP2011-282391.
Office Action dated Sep. 10, 2013 in corresponding Japanese Application No. 2012-212771.
Office Action dated Apr. 24, 2014 in Chinese Patent Application No. 201210579393.7.

* cited by examiner

CHEMICAL LIQUID INJECTION SYSTEM

CROSS-REFERENCE TO RELATED APPLICATIONS

This application is a continuation of U.S. application Ser. No. 10/598,536, now U.S. Pat. No. 7,967,778, filed on Sep. 1, 2006 as the U.S. National Phase under 35 U.S.C. §371 of International application PCT/JP2005/03498, filed Mar. 2, 2005, which claims priority to Japanese Pat. application Ser. No. 2004-059034, filed Mar. 3, 2004, which are hereby incorporated by reference in there entirety.

TECHNICAL FIELD

The present invention relates to a chemical liquid injection system in which a chemical liquid injector injects a liquid in a liquid syringe into a patient, and more particularly, to a chemical liquid injection system for injecting a contrast medium into a patient whose diagnostic images are to be taken by a diagnostic imaging apparatus such as a CT (Computed Tomography) scanner.

BACKGROUND ART

Presently available diagnostic imaging apparatuses for capturing diagnostic images of patients include CT scanners, MRI (Magnetic Resonance Imaging) apparatuses, PET (Positron Emission Tomography) apparatuses, ultrasonic diagnostic apparatuses, CT angiography apparatuses, and MRA (MR angiography) apparatuses. When such a diagnostic imaging apparatus is used, a liquid such as a contrast medium or physiological saline may be injected into a patient. Chemical liquid injectors for automatically performing the injection have been put into practical use.

Such a chemical liquid injector has a liquid injection mechanism includes a driving motor, a slider mechanism and the like, for example. A liquid syringe is removably mounted on the injector. The liquid syringe includes a cylinder member and a piston member slidably inserted in the cylinder member. There are a pre-filled type and a refill type in the liquid syringe.

The liquid syringe of the pre-filled type filled with a liquid within its cylinder member and shipped in wholley sealed by a packing material. In the liquid syringe of the refill type, a user fills a cylinder member with a desired liquid. To simplify the explanation, the following description will be made on the premise that the liquid syringe of the pre-filled type is used.

When the liquid in the abovementioned liquid syringe is injected into a patient, an operator prepares an appropriate liquid syringe for a liquid to be used and takes the liquid syringe out from the packing material. The operator connects the liquid syringe to the patient through an extension tube and sets the syringe on a liquid injection mechanism of a chemical liquid injector. In response to a predetermined operation, the chemical liquid injector relatively moves the piston member and the cylinder member with the liquid injection mechanism to inject the liquid into the patient from the liquid syringe.

In this case, the operator determines the rate at which the liquid is injected and the total quantity of the liquid to be injected in view of the type of the liquid and the like, and then enters data representing the rate and total quantity into the chemical liquid injector. The chemical liquid injector injects the liquid into the patient based on the entered data. For example, when the contrast medium is injected as the liquid, the contrast medium changes the degree of contrast in the patient to allow the diagnostic imaging apparatus to capture a good diagnostic image of the patient.

Some chemical liquid injectors are capable of injecting physiological saline in addition to the contrast media into the patient. In such a chemical liquid injector, the operator enters, as desired, an instruction to inject the physiological saline following the completion of the injection of the contrast medium, together with data representing the injection rate and total quantity of the physiological saline, into the chemical liquid injector.

The chemical liquid injector injects the contrast medium into the patient based on the entered data and then automatically injects the physiological saline. The subsequently injected physiological saline can push the previously injected contrast medium to reduce the consumption of the contrast medium, and also can reduce artifacts in the captured image.

Chemical liquid injectors of the type described above have been devised and applied for patent by the applicant of the present application and the like (see, for example, patent documents 1 and 2 below).

Patent document 1: Japanese laid-open patent publication No. 2002-11096;

Patent document 2: Japanese laid-open patent publication No. 2002-102343.

DISCLOSURE OF THE INVENTION

Subject to be Solved by the Invention

In the abovementioned chemical liquid injector, the liquid can be injected to the patient from the liquid syringe. The operator needs to select an appropriate liquid syringe in order to inject a proper liquid. However, some liquid syringes have the same exterior appearance even when they contain different types of liquid, so that the operator may set a liquid syringe containing an inappropriate liquid on the chemical liquid injector.

In some cases, improperly manufactured liquid syringes may be used, and their inappropriate performance such as low resistance to pressure may cause medical malpractice. The liquid syringe of the pre-filled type is discarded after it is used once in order to prevent infection and the like. For the currently available chemical liquid injectors, however, it is impossible to prevent medical malpractice of reuse of a liquid syringe after it is used once.

When the chemical liquid injector is used, the liquid syringe is typically connected to the patient through an extension tube and a needle-like member such as a catheter. The chemical liquid injector injects a liquid into the patient at a higher pressure than in manual operation. It is thus necessary to use a liquid syringe, an extension tube and the like resistant to the high pressure in the chemical liquid injector, but it is impossible to prevent the use of an improper product as a peripheral tool for the syringe such as the extension tube and the catheter.

As described above, the operator needs to enter data representing the rate and total quantity of the injection of the liquid into the chemical liquid injector. Since the entry operation is complicated and difficult to perform for the operator who is not skilled, the entry of incorrect numeral values is inevitable. Particularly, the currently available contrast media contain active ingredients which differ in concentration several fold at maximum. If correct numeral values are not entered, the patient may be injected with the contrast medium of the quantity which is several times larger than or a fraction of the appropriate quantity.

The operator needs to enter data representing the injection rate or the like into the chemical liquid injector in some cases based on the area to be imaged and the weight of the patient. The operation is also complicated and erroneous entry cannot be prevented. The present applicant has applied Japanese patent application No. 2002-281109 in which a contrast medium is injected at a varying rate to improve an effect of the contrast medium, but it is not easy to set the data representing such a variable pattern in the chemical liquid injector.

To solve the abovementioned problems, the present applicant has applied Japanese patent application No. 2003-098058 in which various types of data are recorded on the packing material of a liquid syringe or the like, for example with a bar code, and the bar code is read by the chemical liquid injector to retrieve the recorded data. However, the bar code can represent only a small amount of data, so that only limited data such as identification data can be recorded.

Thus, in the abovementioned chemical liquid injector, a large amount of data of various types such as the variable pattern is previously registered and retrieved according to the reading of the bar code. However, this requires the previous recording of the various types of data in the chemical liquid injector, and when the recorded data needs to be renewed, the data needs to be updated in the chemical liquid injector.

The present invention has been made in view of the abovementioned problems, and it is an object thereof to provide a chemical liquid injection system in which a large amount of data can be entered easily into the chemical liquid injector to perform various operations.

Means to Solve the Subject

The chemical liquid injection system according to the present invention has a liquid syringe and a chemical liquid injector. The liquid syringe has a cylinder member filled with a liquid and a piston member inserted slidably into the cylinder member and is exchangeably mounted on the chemical liquid injector. The chemical liquid injector has a liquid injection mechanism for relatively moving the cylinder member and the piston member of the liquid syringe to inject the liquid into a patient.

An RFID chip having various types of data recorded thereon is placed on the liquid syringe. The chemical liquid injector has an RFID reader and an operation control means The RFID reader obtains the various types of data recorded on the RFID chip. The operation control means performs a predetermined operation in accordance with at least some of the various types of obtained data. For example, when the RFID chip having a variable pattern for the liquid recorded thereon is put on the liquid syringe, the chemical liquid injector injects the liquid according to the predetermined variable pattern.

Various means referred to in the present invention may be arranged to perform their functions, and may comprise dedicated hardware for performing a predetermined function, a data processing apparatus whose predetermined function is given by a computer program, a predetermined function performed by a data processing apparatus according to a computer program, or a combination thereof.

Various components referred to in the present invention do not need to be a separate entity. A plurality of means may be constructed as one member, a certain means may be part of another means, or a certain means may have a portion overlapping a portion of another means.

Effect of the Invention

In the chemical liquid injection system of the present invention, the RFID chip having the various types of data recorded thereon is put on the liquid syringe. The chemical liquid injector obtains the various types of data recorded on the RFID chip and performs the predetermined operation in accordance with at least some of the various types of data. The variable pattern for the liquid, for example, can be recorded on the RFID chip of the liquid syringe to allow the chemical liquid injector to inject the liquid in accordance with the predetermined variable pattern. In this manner, a large amount of data can be easily input to the chemical liquid injector to perform the various operations.

DESCRIPTION OF REFERENCE NUMERALS

100 CHEMICAL LIQUID INJECTOR
101 INJECTION CONTROL UNIT
104 MAIN TOUCH PANEL SERVING AS DATA DISPLAY MEANS
110 INJECTION HEAD
117 LIQUID INJECTION MECHANISM
121 SUB TOUCH PANEL SERVING AS DATA DISPLAY MEANS
122 RFID READER
140 OPERATION CONTROL MEANS
141 DATA STORING MEANS
142 DATA COLLATING MEANS
143 ALARM OUTPUTTING MEANS
144 DATA ACCUMULATING MEANS
146 DATA HOLDING MEANS
147 DISPLAY CONTROL MEANS
148 INJECTION CONTROL MEANS
200 LIQUID SYRINGE
210 CYLINDER MEMBER
220 PISTON MEMBER
300 MRI APPARATUS SERVING AS DIAGNOSTIC IMAGING APPARATUS
1000 CHEMICAL LIQUID INJECTION SYSTEM

BEST MODE FOR CARRYING THE INVENTION (Configuration of Embodiment)

An embodiment of the present invention will hereinafter be described with reference to drawings. As shown in FIGS. 1 to 4, chemical liquid injection system 1000 of the embodiment according to the present invention comprises chemical liquid injector 100, liquid syringe 200, and MRI apparatus 300 which is a diagnostic imaging apparatus. The system is provided for injecting a contrast media or the like as a liquid into a patient (not shown), as later described in detail.

Figure 4:
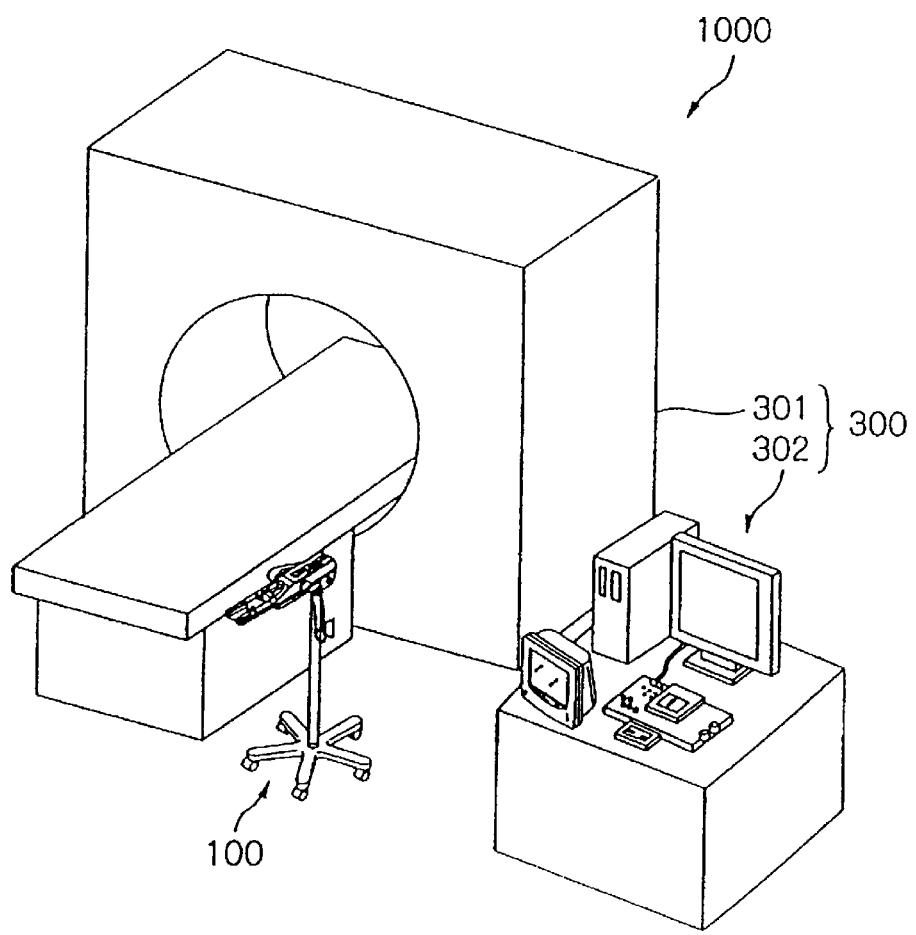
FIG. 4 is a perspective view showing the exterior appearance of an MRI apparatus serving as a diagnostic imaging apparatus.

As shown in FIG. 4, MRI apparatus 300 includes diagnostic imaging unit 301 serving as a mechanism for performing imaging and imaging control unit 302 such that diagnostic imaging unit 301 and imaging control unit 302 are wire-connected through communication network 303. Diagnostic imaging unit 301 shoots a diagnostic image of a patient. Imaging control unit 302 controls the operation of diagnostic imaging unit 301.

Figure 2:
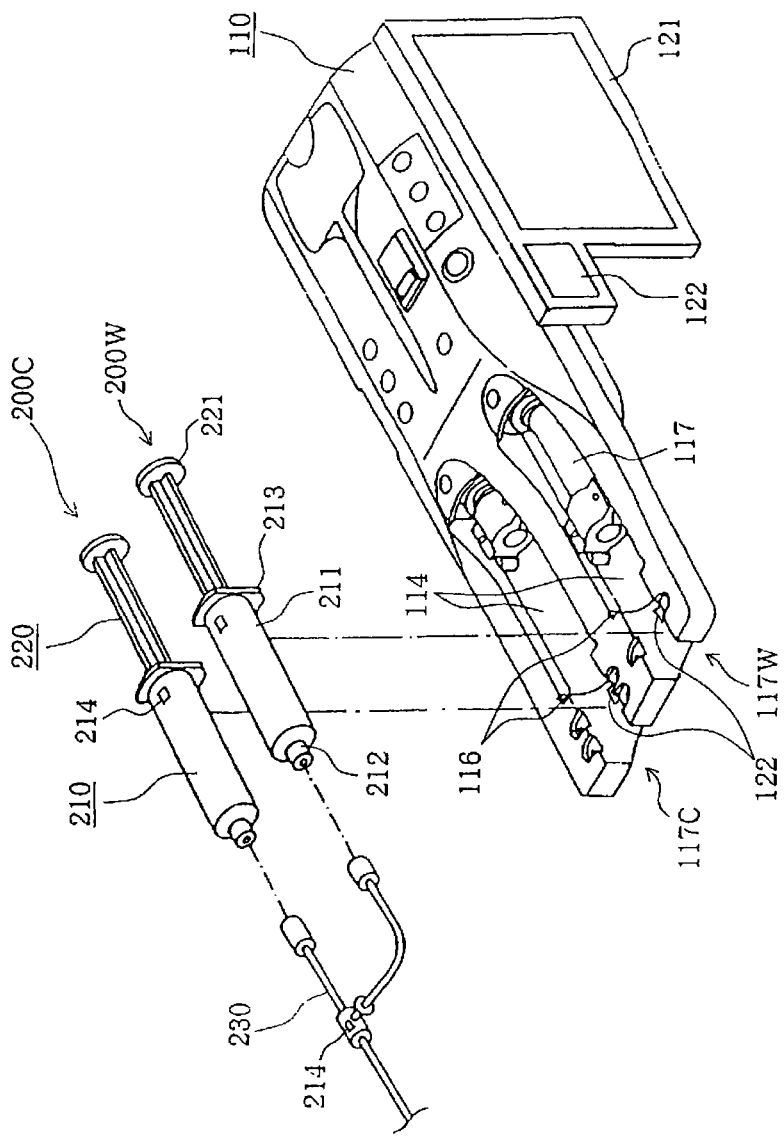
FIG. 2 is a perspective view showing how a liquid syringe is mounted on an injection head of the chemical liquid injector.

As shown in FIG. 2, liquid syringe 200 comprises cylinder member 210 and piston member 220 wherein piston member 220 is slidably inserted into cylinder member 210. Cylinder member 210 includes cylindrical hollow body 211 which has conduit 212 formed at the closed leading end.

The trailing end of body 211 of cylinder member 210 is opened and piston member 220 is inserted from the opening into the interior of body 211. Cylinder member 210 has cylinder flange 213 formed in the outer circumference of the trailing end, and piston member 220 has piston flange 221 formed in the outer circumference of the trailing end.

In chemical liquid injection system 1000 of the embodiment, at least some of liquid syringes 200 to be used are of the pre-filled type. Liquid syringe 200 of the pre-filled type is shipped with cylinder member 210 filled with a liquid.

RFID chip 214 is placed on cylinder member 210 of liquid syringe 200. RFID chip 214 has various types of data about liquid syringe 200 recorded thereon such as the name, the identification data indicating the pre-filled type or the refill type, the identification data for each item, the capacity, the resistance to pressure of cylinder member 210, the inner diameter of cylinder member 210, and the stroke of piston member 220.

When liquid syringe 200 of the pre-filled type is used, RFID chip 214 also has various types of data about the contained liquid set thereon such as the name, the ingredients, the viscosity, the expiration date, and the identification data indicating whether the liquid is for CT or MR. When a contrast medium is contained as the liquid in liquid syringe 200 of the pre-filled type, RFID chip 214 also has data set thereon, as required, such as the variable pattern of varying an injection rate with time.

Liquid syringes 200 include contrast medium syringe 200C filled with the contrast medium as the liquid and physiological saline syringe 200W filled with physiological saline as the liquid. Contrast medium/physiological saline syringes 200C and 200W are mounted simultaneously on chemical liquid injector 100.

Contrast medium/physiological saline syringes 200C and 200W mounted on chemical liquid injector 100 are connected to a patient through a peripheral device for the syringe such as bifurcated extension tube 230. RFID chip 214 is also placed on such a peripheral device and has various types of data recorded thereon such as the name and the resistance to pressure of the peripheral device.

Figure 3:
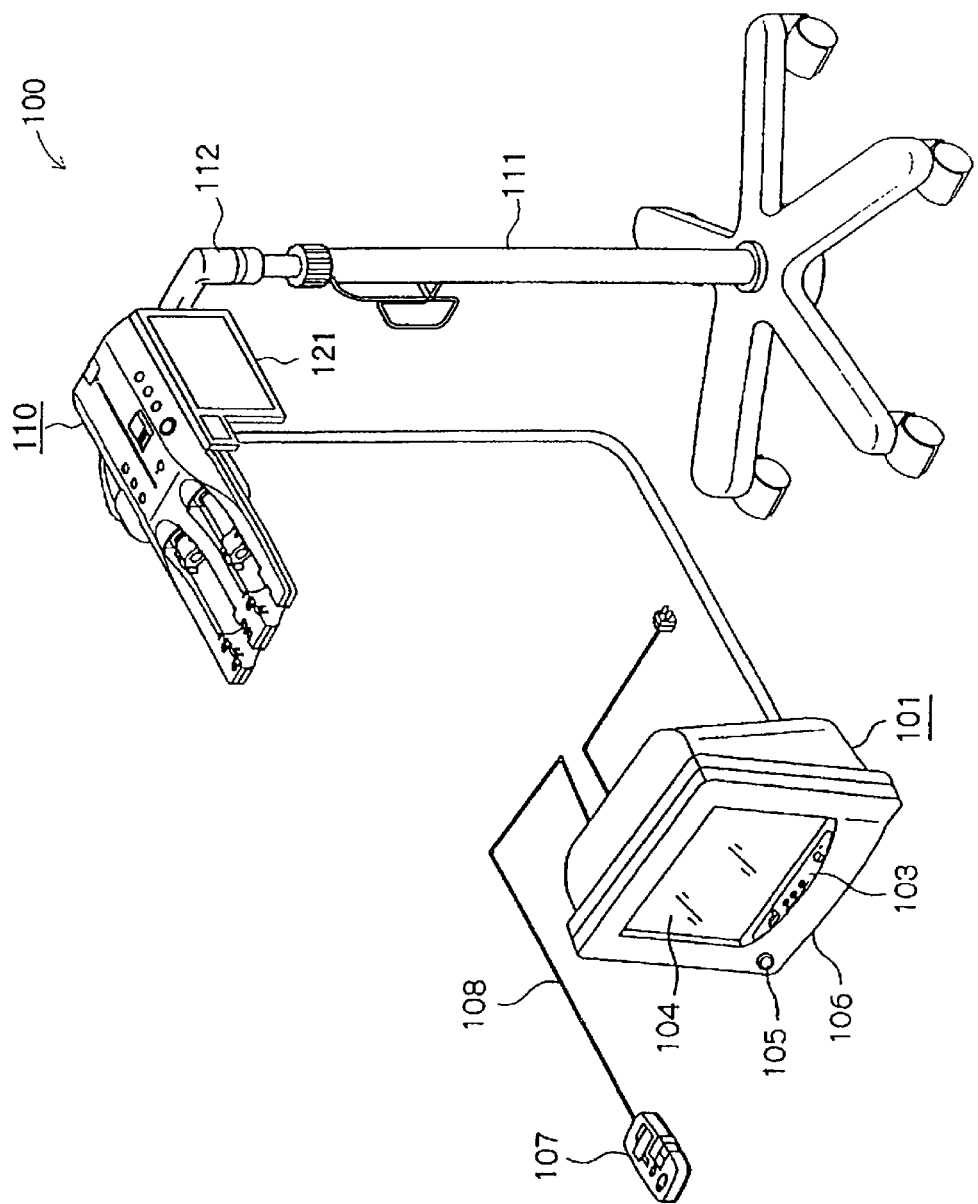
FIG. 3 is a perspective view showing the exterior appearance of the chemical liquid injector.

As shown in FIG. 3, chemical liquid injector 100 of the embodiment has injection control unit 101 and injection head 110 constructed as separate components which are wire-connected through communication cable 102.

Figure 5:
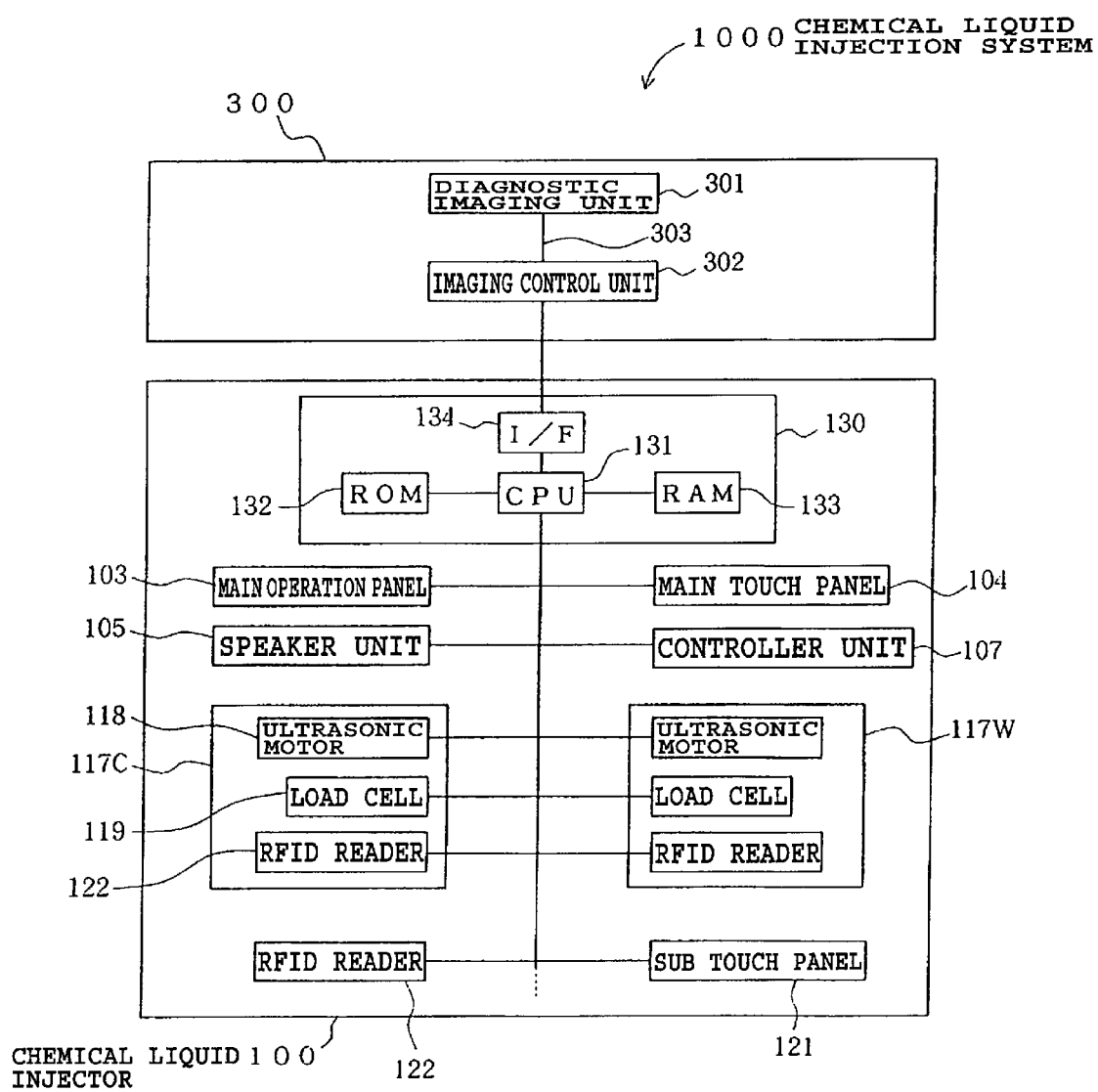
FIG. 5 is a block diagram showing the circuit structure of the chemical liquid injector.

Injection head 110 drives liquid syringe 200 mounted thereon to inject a liquid therefrom into a patient. Injection control unit 101 controls the operation of injection head 110. Thus, as shown in FIG. 5, injection control unit 101 has computer unit 130 and is wire-connected to imaging control unit 302 of MRI apparatus 300 through communication network 304.

Injection control unit 101 has main operation panel 103, main touch panel 104 serving as a data display means, and speaker unit 105, all of which are disposed on the front face of unit housing 106. Injection control unit 101 is wire-connected to controller unit 107 as a separate component through connector 108.

Injection head 110 is attached to the top end of caster stand 111 by movable arm 112. As shown in FIG. 2, head body 113 of injection head 110 has concave portion 114 formed as a semi-cylindrical groove in the upper surface for removably mounting liquid syringe 200.

Cylinder holding mechanism 116 is formed in the forward section of concave portion 114 for removably holding cylinder flange 213 of liquid syringe 200. Liquid injection mechanism 117 is arranged in the rearward section of concave portion 114 for holding and sliding piston flange 221.

Cylinder holding mechanism 116 is formed in concave portion 114 as a different-shaped reentrant groove, with which cylinder flange 213 removably engages. Liquid injection mechanisms 117 individually have ultrasonic motor 118 as driving sources which are free from generation of magnetic field even in operation, and slide piston members 220 through screw mechanisms (not shown) or the like. Load cells 119 are also contained in liquid injection mechanism s117 and detect the pressure applied to piston members 220.

Since contrast medium/physiological saline syringes 200C and 200W are individually put in two concave portions 114 of injection head 110, two concave portions 114 and two liquid injection mechanisms 117 constitute contrast medium injection mechanism 117C for injecting the contrast medium and physiological saline injection mechanism 117W for injecting the physiological saline into the patient.

Cylinder flange 213 of liquid syringe 200 is not in a simple ring shape but formed as an oval shape with two parallel sides on its outer edge. Cylinder holding mechanism 116 holds cylinder flange 213 of liquid syringe 200 in a predetermined direction to prevent rotation, so that each liquid syringe 200 has a pair of RFID chips 214 placed thereon at the upper and lower positions when it is held as described above.

RFID readers 122 are placed at a predetermined position of concave portions 114 of injection head 110. RFID readers 122 obtain various types of data from RFID chips 214 of liquid syringes 200 which are put in concave portions 114 and held by cylinder holding mechanisms 116.

Sub touch panel 121 serving as a data display means and RFID reader 122 are attached to the side of the rearward section of injection head 110. RFID reader 122 obtains various types of data from RFID chips 214 on liquid syringe 200 and extension tube 230.

In chemical liquid injector 100 of the embodiment, respective components of injection head 110 are formed of nonmagnetic material, and the portions which cannot be formed of nonmagnetic material are magnetically shielded. For example, ultrasonic motor 118 and load cell 119 are formed of nonmagnetic metal such as phosphor bronze alloy (Cu+Sn+P), titanium alloy (Ti-6Al-4V), and magnesium alloy (Mg+Al+Zn). Head body 113 or the like is formed of nonmagnetic resin.

As shown in FIG. 5, in chemical liquid injector 100 of the embodiment, the abovementioned various devices are connected to computer unit 130 which comprehensively controls those various devices. Computer unit 130 is formed of a so-called one-chip microcomputer provided with hardware such as CPU (Central Processing Unit) 131, ROM (Read Only Memory) 132, RAM (Random Access Memory) 133, I/F (Interface) 134 and the like.

Computer unit 130 has an appropriate computer program installed as firmware or the like in an information storage medium such as ROM 132, and CPU 131 executes various types of processing in accordance with the computer program.

Figure 1:
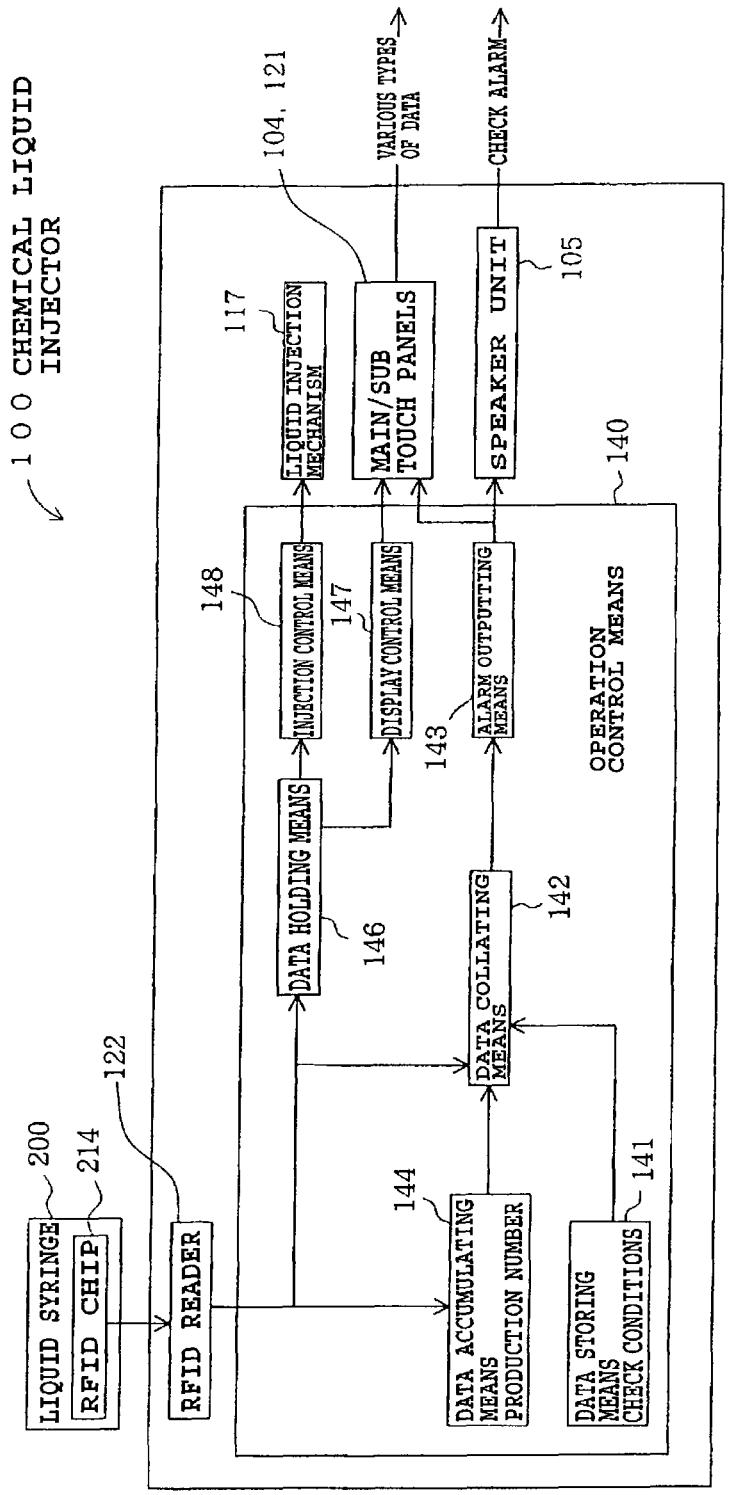
FIG. 1 is a schematic block diagram showing the logical configuration of a chemical liquid injector according to an embodiment of the present invention.

Computer unit 130 operates in accordance with the computer program installed as described above to allow chemical liquid injector 100 of the embodiment to logically have operation control means 140 as shown in FIG. 1. Operation control means 140 logically has various means such as data storing means 141, data collating means 142, alarm outputting means 143, data accumulating means 144, data holding means 146, display control means 147, and injection control means 148.

Operation control means 140 corresponds to the function of CPU 131 which performs predetermined operations in accordance with the computer program installed in ROM 132 or the like and the various types of data obtained from RFID chip 214. Operation control means 140 has data storing means 141, data collating means 142, alarm outputting means 143, data accumulating means 144, data holding means 146, display control means 147, and injection control means 148.

Data storing means 141 corresponds to the store area of RAM 133 and the like recognized by CPU 131 and stores predetermined check conditions as data. Data collating means 142 collates the check conditions stored as data with the various types of data obtained from RFID chip 214. Alarm outputting means 143 outputs and notifies a check alarm in accordance with the collation result.

More particularly, RAM 133 has data for identifying usable liquid syringe 200 and extension tube 230 registered thereon as the check conditions. When RFID reader 122 obtains various types of data from RFID chip 214 of liquid syringe 200 or extension tube 230, the obtained identification data of liquid syringe 200 or extension tube 230 is collated with the identification data registered in RAM 133.

When the obtained identification data is not registered, a guidance message as "This product is not registered as usable device. Check if it is usable" is output as a check alarm with display on main/sub touch panels 104 and 121 and with sound from speaker unit 105.

The current date and time is constantly updated and held in the check conditions on RAM 133. When the expiration date is obtained from RFID chip 214 of liquid syringe 200, the expiration date is collated with the current date and time. If the current data and time is after the expiration date, a guidance message as "Expiration date of this product elapsed. Use new one" is output as a check alarm with display on main/sub touch panels 104 and 121 and with sound from speaker unit 105.

The production number of each liquid syringe 200 of the pre-filled type is set on RFID chip 214. Data accumulating means 144 stores the data of the production number of liquid syringe 200 of the pre-filled type which was put on injection head 110 and used to perform injection operation.

Data collating means 142 collates the stored production number with a production number obtained from RFID chip 214. When the collated production numbers match, alarm outputting means 143 outputs a guidance message as "This pre-filled syringe is used previously. Use new one" as a check alarm with display on main/sub touch panels 104 and 121 and with sound from speaker unit 105.

Data holding means 146 holds various types of data obtained from RFID chip 214. Display control means 147 displays the held various types of data on main/touch panels 104 and 121. Injection control means 148 controls the operation of liquid injection mechanism 117 based on the held various types of data.

More specifically, RFID chip 214 of liquid syringe 200 has various types of data recorded thereon such as the name, the resistance to pressure, and the capacity of liquid syringe 200 as well as the name, the ingredients, and the expiration date of the liquid in liquid syringe 200. The various types of data are temporarily stored in RAM 133 and output with display on main/sub touch panels 104 and 121.

When the control data for liquid injection mechanism 117 is set on RFID chip 214 of liquid syringe 200, the control data is held in RAM 133 and CPU 131 controls the operation of liquid injection mechanism 117 based on the held control data. For example, when a variable pattern for changing the injection rate of the contrast medium with time is recorded as data in RFID chip 214 of contrast medium syringe 200C, CPU 131 changes the operation rate of contrast medium injection mechanism 117C with time in accordance with the variable pattern.

When the resistance to pressure is recorded as data on RFID chip 214 of liquid syringe 200 or extension tube 230, CPU 131 controls the operation of liquid injection mechanism 117 such that the resistance to pressure held as data in RAM 133 is not exceeded on the basis of the pressure detected by load cell 119.

When the capacity is recorded as data on RFID chip 214 of liquid syringe 200, CPU 131 controls the operation of liquid injection mechanism 117 based on the capacity held as data on RAM 133. When the identification data of the liquid is obtained from RFID chips 214 of contrast medium syringe 200C and physiological saline syringe 200W, CPU 131 sequentially activates contrast medium injection mechanism 117C and physiological saline injection mechanism 117W.

The above various means of chemical liquid injector 100 are accomplished by pieces of hardware such as main/sub touch panels 104 and 121 as required. They are mainly implemented by CPU 131 as a piece of hardware functioning in accordance with resources and computer program stored on an information storage medium such as ROM 132.

Such a computer program is stored in an information storage medium such as RAM 133 as software for causing CPU 131 or the like to perform processing operations including steps of collating the check conditions stored as data in RAM 133 and the like with the various types of data obtained from RFID chip 214 when RFID reader 122 obtains the various types of data from RFID chip 214; outputting the check alarm with data display on main/sub touch panels 104 and 121 in accordance with the collation result; storing the production number of liquid syringe 200 mounted and used to perform injection operation in RAM 133 or the like; collating the stored production number with the production number obtained as data from RFID chip 214; outputting the check alarm with data display on main/sub touch panels 104 and 121 in accordance with the collation result; holding the various types of data obtained from RFID chip 214 on RAM 133 or the like; displaying the held various types of data on main/sub touch panels 104 and 121; and controlling the operation of liquid injection mechanism 117 in accordance with the held various types of data.

(Operation of the Embodiment)

When chemical liquid injector 100 of the embodiment is used in the abovementioned structure, chemical liquid injector 100 is placed near imaging unit 301 of MRI apparatus 300, and contrast medium/physiological saline syringes 200C and 200W and extension tube 230 are prepared for use as shown in FIG. 3.

Then, a guidance message for selection of an operation mode is output with display on main/sub touch panels 104 and 121 of chemical liquid injector 100 as "Select operation mode. 1. Inject contrast medium and physiological saline. 2. Inject only contrast medium. 3. Inject only physiological saline." An operator makes entry to set a selected operation mode into chemical liquid injector 100 (steps S1 and S2).

In chemical liquid injector 100 of the embodiment, when the operation mode is entered as described above, the data about the devices to be used such as contrast medium syringe 200C and extension tube 230 are set. Injection operation is not started (step S11 and subsequent steps) unless various types of data are obtained from all of RFID chips 214 of the devices to be used (steps S3 to S10).

For example, when "1. Inject contrast medium and physiological saline" is selected as the operation mode, contrast medium syringe 200C, physiological saline syringe 200W, extension tube 230, and an injection needles (not shown) are set as devices to be used. The operator sequentially faces RFID chips 214 of extension tube 230 and the injection needle toward RFID reader 122 on the side of injection head 110 and mounts contrast medium/physiological saline syringes 200C and 200W on contrast medium/physiological saline injection mechanisms 117C and 117W of injection head 110.

When RFID chip 214 of extension tube 230 or the like is faced toward RFID reader 122 of injection head 110, RFID reader 122 obtains various types of data from RFID chip 214 (step S3) and collates the data with check conditions registered in RAM 133 of computer unit 130 (step S4).

Such check conditions include the identification data of usable liquid syringe 200, usable extension tube 230 or the like. If the identification data obtained from RFID chip 214 is not included in the check conditions, a guidance message as "This product not registered as usable device. Check if is usable" is output as a check alarm with display on main/sub touch panels 104 and 121 and with sound from speaker unit 105 (step S5).

When contrast medium/physiological saline syringes 200C and 200W are appropriately mounted on contrast medium/physiological saline injection mechanisms 117C and 117W, RFID chips 214 thereof are naturally faced toward RFID reader 122 with a predetermined interval between them, so that various types of data of RFID chips 214 are obtained by RFID reader 122 (step S3).

The obtained data is also collated with the check conditions (step S4), and a check alarm is output (step S5) if the obtained identification data is not included in the check conditions. Even after the data matches the check conditions, when it is determined that the device to be used is liquid syringe 200 (step S6), the production number obtained from RFID chip 214 thereof is collated with the production number registered in RAM 133 (step S7).

When the collated production numbers match, a guidance message as "This syringe is used previously. Use new one" is output as a check alarm on main/sub touch panels 104 and 121 and from speaker unit 105 (step S5).

The various types of data obtained from RFID chip 214 of the appropriate device into chemical liquid injector 100 as described above are output with display on main/sub touch panels 104 and 121, for example as "This is extension tube (name) made by (manufacturer) with resistance to pressure XXX," or "Contrast medium syringe (name) made by (manufacturer) mounted. Production number XXX, name of liquid XXX, type of liquid XXX, capacity XXX, resistance to pressure XXX" (step S8).

RFID chip 214 has various types of data to be displayed and various types of data not to be displayed. For example, a binary flag is set in each data to indicate whether or not the data should be displayed. Chemical liquid injector 100 appropriately selects some of the various types of data obtained from RFID chip 214 for display.

When the various types of data obtained from RFID chip 214 of the device into chemical liquid injector 100 include control data such as "resistance to pressure," "capacity," and "variable pattern for changing the injection rate of the contrast medium with time," the control data is set in RAM 133 of computer unit 130 (step S9). When such control data is not included in the data obtained from RFID chip 214, default control data is set.

As described above, contrast medium/physiological saline syringes 200C and 200W mounted on chemical liquid injector 100 is connected to a patient through extension tube 230 and then the operator makes entry to start operation to main/sub touch panels 104 and 121 or main operation panel 103. Then, chemical liquid injector 100 detects the entry (step S11) and transmits data for starting operation to MRI apparatus 300 (step S14).

Figure 8:
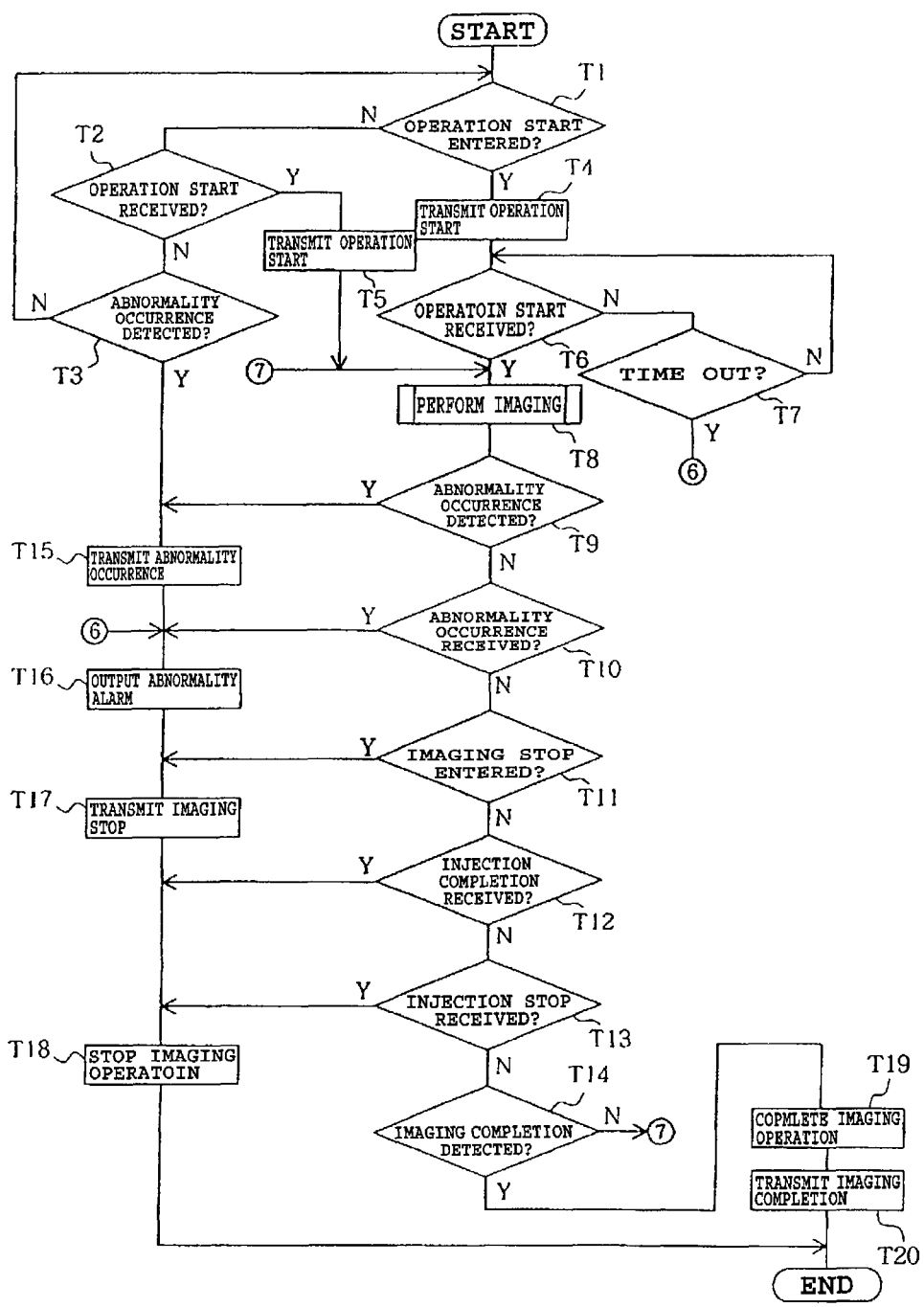
FIG. 8 is a flow chart showing processing operation of the MRI apparatus.

As shown in FIG. 8, MRI apparatus 300 receives the data for staring operation from chemical liquid injector 100 (step T2) and sends the data for starting operation back to chemical liquid injector 100 and performs imaging operation (step T8). Thus, in diagnostic imaging system 1000 of the embodiment, the imaging of MRI apparatus 300 follows the liquid injection of chemical liquid injector 100.

Figure 6:
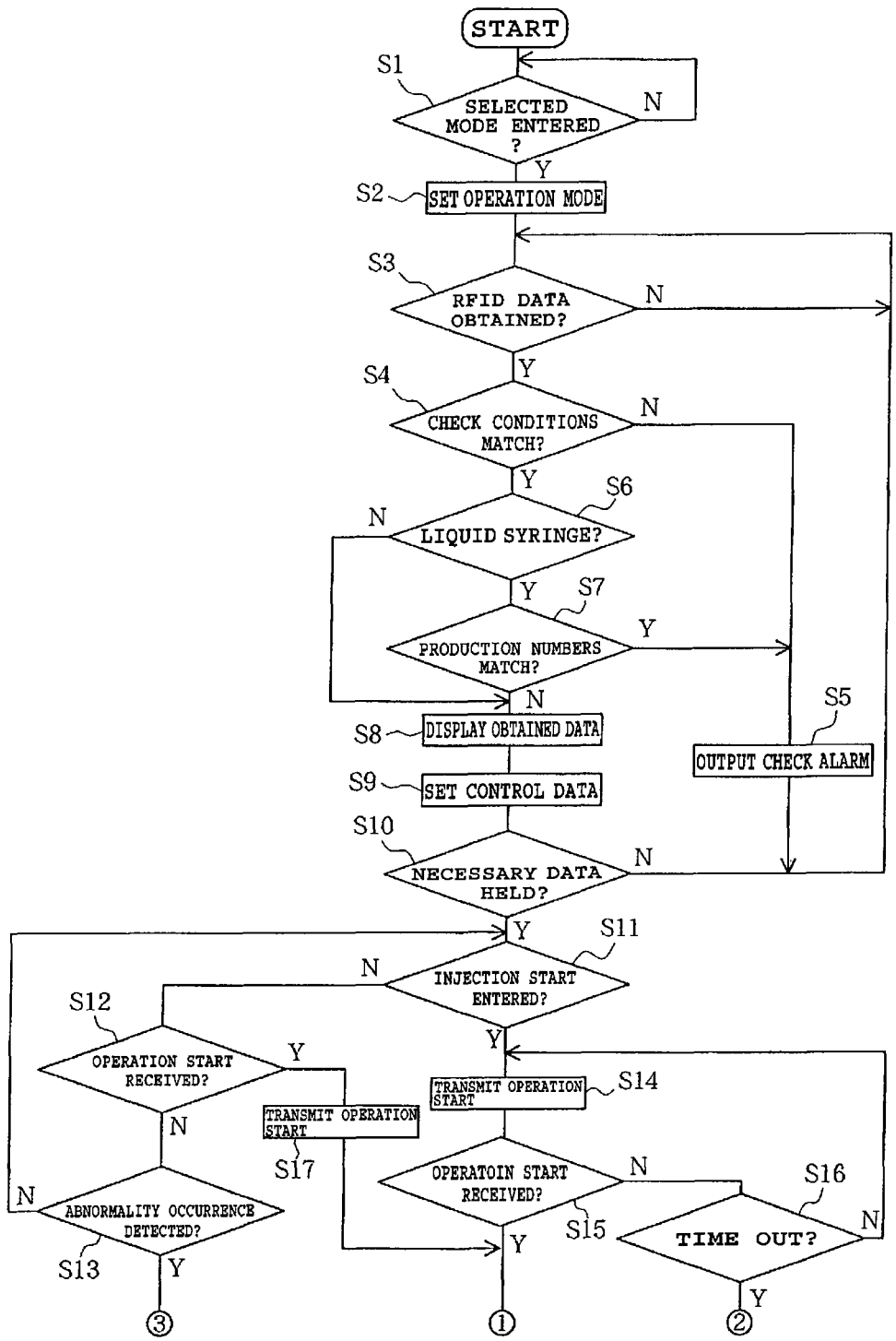
FIG. 6 is a flow chart showing the first half of processing operation of the chemical liquid injector.

As shown in FIGS. 6 and 8, in diagnostic imaging system 1000 of the embodiment, when chemical liquid injector 100 is ready as described above (steps S11 to S13) and the operator makes entry to start operation to MRI apparatus 300 (step T1), the liquid injection of chemical liquid injector 100 follows the imaging of MRI apparatus 300 (steps T4, T6 and subsequent steps, steps S12, S18 and subsequent steps).

Figure 7:
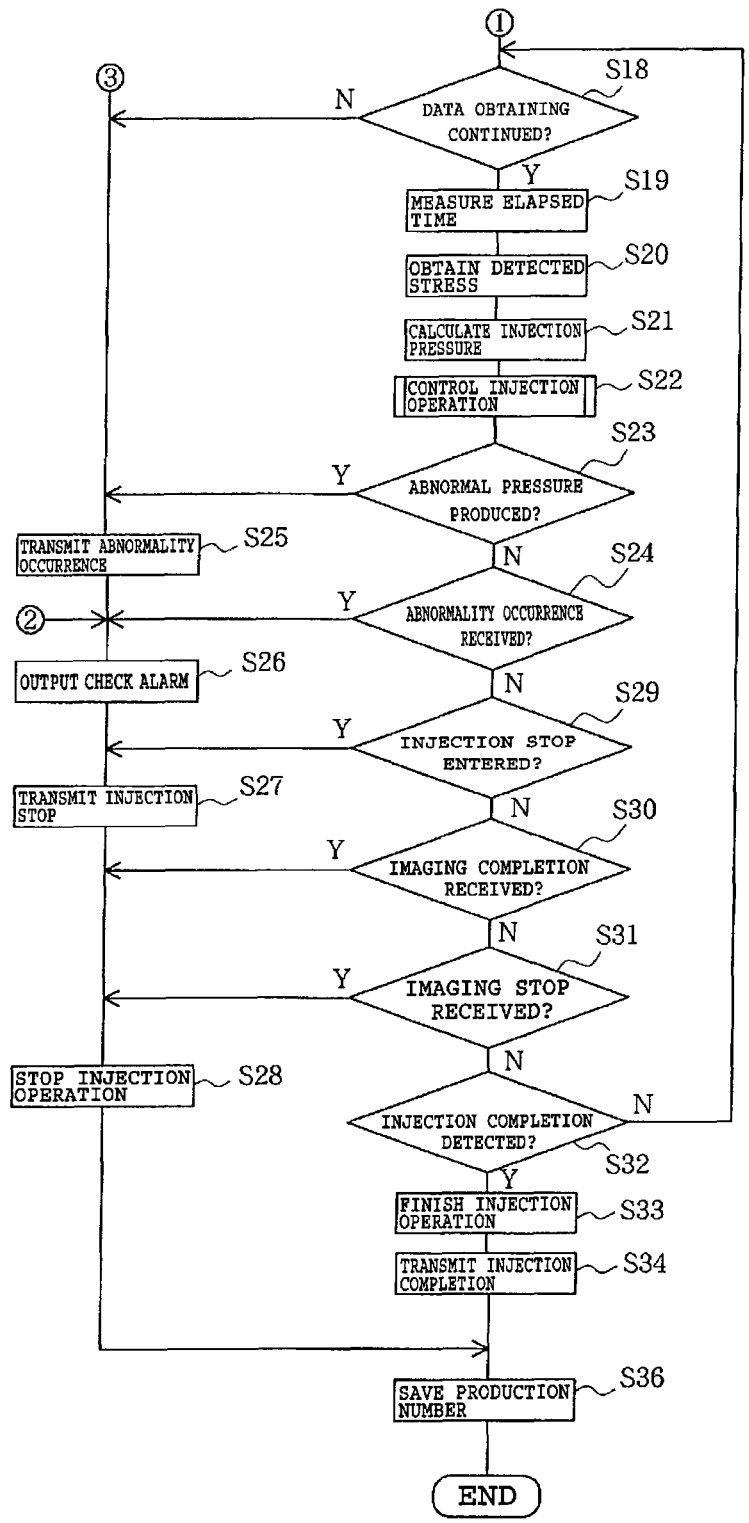
FIG. 7 is a flow chart showing the latter half of the processing operation of the chemical liquid injector.

As shown in FIG. 7, when a series of liquid injection operations is performed (step S18 and subsequent steps) in chemical liquid injector 100 of the embodiment, the elapsed time from the start of the injection is measured (step S19), and the operations of contrast medium injection mechanism 117C and physiological saline injection mechanism 117W are controlled sequentially in real time based on the elapsed time and the control data obtained from RFID chip 214 (step S22).

When the variable pattern for changing the injection rate of the contrast medium with time is set in RFID chip 214 of contrast medium syringe 200C, the operation rate of contrast medium injection mechanism 117C is changed with time in accordance with the variable pattern. When the injection pattern for starting injection of physiological saline in response to the completion of the injection of the contrast medium is set in RFID chip 214 of physiological saline syringe 200W, the operation of physiological saline injection mechanism 117W is controlled in accordance with the injection pattern.

When "1. Inject contrast medium and physiological saline" is set as the operation mode, both of contrast medium/physiological saline injection mechanisms 117C and 117W are driven. When "2. Inject only contrast medium" is set, only contrast medium injection mechanisms 117C is driven. When "3. Inject only physiological saline" is set, only physiological saline injection mechanisms 117W is driven.

When liquid injection mechanism 117 is driven as described above, the stress detected by load cell 119 is input in real time to computer unit 130 (step S20). Based on the viscosity of the liquid and the inner diameter of cylinder member 210 obtained from RFID chip 214, the injection pressure of the liquid is calculated from the stress detected by load cell 119 (step S21), and the operation of liquid injection mechanism 117 is controlled in real time such that the calculated injection pressure comply with the pressure range obtained from RFID chip 214 (step S23).

When the resistance to pressure is set in RFID chips 214 of contrast medium/physiological saline syringe 200C and 200W and extension tube 230, the operation of contrast medium/physiological saline injection mechanisms 117C and 117W are controlled on the basis of the resistance to pressure. If the plurality of devices have different resistances to pressure, the operation is controlled on the basis of the lowest resistance to pressure as a matter of course.

While contrast medium/physiological saline syringes 200C and 200W are driven by contrast medium/physiological saline injection mechanisms 117C and 117W as described above, RFID reader 122 continuously detects RFID chips 214 (step S18). If the abovementioned detection is stopped (step S18) before the injection operation is completed (step S32), the injection operation performed by contrast medium/physiological saline injection mechanisms 117C and 117W is stopped (step S28).

In addition, a guidance message as "Syringe removal is detected. Make sure syringe is put appropriately" is output as a check alarm with display on main/sub touch panels 104 and 121 and with sound from speaker unit 105 (step S26). The occurrence of abnormality and the stop of injection are transmitted as data to MRI apparatus 300 (steps S25 and S28).

Then, MRI apparatus receives the data representing the occurrence of abnormality (step T10) and outputs the occurrence of abnormality as a check alarm with guidance display or the like (step S16). When it receives the data representing the stop of operation (step T13), the imaging operation is stopped (step S18).

In chemical liquid injector 100 and MRI apparatus 300 of the embodiment, when the occurrence of abnormality is detected in the abovementioned ready state (steps S13 and T3) or when the occurrence of abnormality is detected during the operation (steps S23 and T9), the occurrence of abnormality is output and notified (steps S26 and T16) and the operation is stopped (steps S28 and T18).

Since the occurrence of abnormality in one of them is transmitted to the other (steps S25 and T15), the other receives the data (steps T10 and S24) and then outputs and notifies the occurrence of abnormality (steps S16 and S26). Since the operation stop in one of them is transmitted to the other (steps S27 and T17), the other receives the data (steps T13 and S31) and stops the operation (steps S18 and S28).

When one of them receives entry to stop operation (steps S29 and T11), the one stops the operation (steps S28 and T18) and transmits it to the other (steps S27 and T17). The other receives the data (steps S13 and S31) and stops the operation (steps S18 and S28).

When the completion of the operation is detected in one of them (steps S32 and T14), the operation is ended (steps S33 and T19) and the end of the operation is transmitted to the other (steps S34 and T20). The other receives the data (steps T12 and S31) and stops the operation (steps T18 and S28).

In chemical liquid injector 100 of the embodiment, when the injection operation is finished normally or abnormally as described above (steps S33 and S28), the identification data obtained from RFID chip 214 of the device such as liquid syringe 200 and extension tube 230 is registered as the check condition in RAM 133 (step S36).

(Effect of the Embodiment)

In chemical liquid injection system 1000 of the embodiment, RFID chip 214 having the various types of data recorded thereon is placed on liquid syringe 200 as described above. Chemical liquid injector 100 obtains the various types of data from RFID chip 214 and performs the predetermined operation in accordance with at least some of the various types of data. In this manner, a large amount of data can be easily entered into chemical liquid injector 100 to perform various operations.

In chemical liquid injection system 1000 of the embodiment, at least some of the various types of data obtained from RFID chip 214 are output with display on main/sub touch panels 104 and 121, so that the operator can check the various types of data of liquid syringe 200 and the like easily and reliably.

Chemical liquid injector 100 of the embodiment has RFID reader 122 placed in concave portion 114 of injection head 110. When liquid syringe 200 is appropriately put in concave portion 114, RFID chip 214 of liquid syringe 200 faces RFID reader 122.

Thus, when liquid syringe 200 is mounted on chemical liquid injector 100, RFID chip 214 of liquid syringe 200 is automatically detected by RFID reader 122, so that RFID chip 214 of liquid syringe 200 can be read by RFID reader 122 of chemical liquid injector 100 readily and reliably.

In chemical liquid injector 100 of the embodiment, computer unit 130 allows liquid injection mechanism 117 to operate only when RFID reader 122 detects RFID chip 214. If liquid syringe 200 comes off the appropriate position during the liquid injection, the liquid injection operation can be stopped automatically.

Since the mechanism for detecting the removal of liquid syringe 200 comprises RFID chip/reader 214 and 122 for transferring the various types of data from liquid syringe 200 to chemical liquid injector 100, the removal of liquid syringe 200 can be detected by using the simple structure without requiring a dedicated sensor mechanism.

Since chemical liquid injector 100 of the embodiment also includes RFID reader 122 on the side of injection head 110, that RFID reader 122 can easily obtain the various types of data from RFID chip 214 of the peripheral device for the syringe such as extension tube 230 even when liquid syringe 200 is mounted on injection head 110.

Sub touch panel 121 is placed on the side of injection head 110. When the operator puts liquid syringe 200 in concave portion 114 of injection head 110 or faces extension tube 230 toward RFID reader 122 on the side of injection head 110, the various types of data are output and displayed on nearby sub touch panel 121 and the operator can check the various types of data of liquid syringe 200 or the like easily and instinctively.

Furthermore, sub touch panel 121 which displays the various types of data obtained from RFID chip 214 also receives entry operation. When chemical liquid injector 100 performs various types of operations based on the various types of data obtained from RFID chip 214, the operator can easily adjust the various types of operation as required.

Chemical liquid injector 100 of the embodiment collates the check conditions stored as data with the various types of data obtained from RFID chip 214, and as required, outputs the check alarm. Thus, for example, when the operator attempts to use liquid syringe 200 which is not allowed in chemical liquid injector 100 or liquid syringe 200 with the expiration date elapsed, the check alarm can be output to prevent any medical malpractice reliably.

In chemical liquid injector 100 of the embodiment, when the data is read from RFID chip 214 of liquid syringe 200 or extension tube 230, the production number of each item is stored. If the production number newly obtained from RFID chip 214 is already stored, the check alarm is output. It is thus possible to readily and reliably prevent medical malpractice such as repeated use of liquid syringe 200 or extension tube 230 which should be discarded after they are used once.

In chemical liquid injection system 1000 of the embodiment, when the variable pattern for changing the injection rate of the constant medium with time is recorded on RFID chip 214 of liquid syringe 200 of the pre-filled type filled with the contrast medium, chemical liquid injector 100 changes the injection rate of the contrast medium with time in accordance with the variable pattern.

Consequently, the optimal degree of contrast can be maintained favorably, and the minimum amount of the injected contrast medium can be used to reduce physical burdens on the patient. In addition, it is not necessary to previously register the data of the complicated variable pattern in chemical liquid injector 100. For example, a new variable pattern for a new contrast medium can be simply input to chemical liquid injector 100 from RFID chip 214 of liquid syringe 200.

In chemical liquid injector 100 of the embodiment, the pressure of the injected liquid is detected from the stress on piston member 220 of liquid syringe 200, and if the injection pressure reaches an abnormal value, the check alarm is output and the injection operation is forcedly stopped. This can prevent medical malpractice of injection of the liquid at an abnormal pressure.

The determination of the pressure of the liquid by chemical liquid injector 100 as described above requires not only the pressure on piston member 220 of liquid syringe 200 but also the various types of data such as the internal diameter of cylinder member 210 and the viscosity of the liquid. The various types of data are input to chemical liquid injector 100 from RFID chip 214. Thus, chemical liquid injector 100 of the embodiment can appropriately detect the injection pressure of each liquid of each liquid syringe 200 without requiring complicated operations of manual entry of the various types of data into chemical liquid injector 100 by the operator.

In addition, in chemical liquid injection system 1000 of the embodiment, RFID chip 214 is placed not only on liquid syringe 200 but also on the peripheral device for the syringe such as extension tube 230. Chemical liquid injector 100 can control the injection operation based on the resistance to pressure of extension tube 230 or the like to prevent advantageously medical malpractice of use of extension tube 230 which is not allowed in chemical liquid injector 100, for example.

In diagnostic imaging system 1000 of the embodiment, since the liquid injection in chemical liquid injector 100 is automatically associated with the imaging in MRI apparatus 300, the diagnostic images can be taken in an appropriate timing from the patient injected with the contrast medium and physiological saline in an appropriate timing.

(Modifications of the Embodiment)

The present invention is not in any way limited to the abovementioned embodiment, but various changes and modifications may be made therein without departing from the scope of the invention. For example, in the above embodiment, RFID reader 122 for obtaining the various types of data from RFID chip 214 and sub touch panel 121 for displaying the obtained data are mounted on injection head 110 in which liquid syringe 200 is put, thereby achieving ease of use.

However, RFID reader 122 and sub touch panel 121 may be disposed at positions away from injection head 110. RFID reader 122 may be formed as a separate portable unit connected to chemical liquid injector 100 through wired or wireless communication (not shown).

For example, the above embodiment has assumed that RFID chip/reader 214 and 122 have coverage of several centimeters for wireless communication and the data on RFID chip 214 is obtained only when RFID chip 214 is faced toward RFID reader 122 at a short distance. However, it is possible that the coverage of several tens of centimeters is set for wireless communication and RFID reader 122 is mounted on movable arm 122 and placed near injection head 110 (not shown).

In this case, when liquid syringe 200 is put in injection head 110 or extension tube 230 is connected to that liquid syringe 200, RFID chip 214 thereof is naturally located at a position where it can wirelessly communicate with RFID reader 122. In such an arrangement, since one RFID reader 122 can communicate with a plurality of RFID chips 214, a simpler structure can be realized.

In the above embodiment, RFID chip 214 is placed on the outer circumference of cylinder member 210 of liquid syringe 200. For example, RFID chip 214 may be placed on the outer surface or the end surface of piston member 220 (not shown).

To simplify the description, the above embodiment shows that liquid syringe 200 having RFID chip 214 placed thereon is directly put in chemical liquid injector 100 on which RFID reader 122 is mounted. However, in currently available chemical liquid injectors 100, only liquid syringe 200 of the largest size is directly mounted, and each of liquid syringes 200 of the sizes other than the largest size is mounted via a dedicated cylinder adapter (not shown).

RFID reader 122 may be placed on the cylinder adapter. In this case, when the cylinder adapter is mounted on injection head 110, RFID reader 122 may be connected to chemical liquid injector 100 (not shown). It is also possible that RFID chip 214 is placed on the cylinder adapter, and when liquid syringe 200 is mounted on injection head 110 with the cylinder adapter, RFID reader 122 of injection head 110 detects the data of RFID chips 214 of liquid syringe 200 and the cylinder adapter (not shown).

In the above embodiment, to use liquid syringe 200 or the like only once, the data of the production number of each of liquid syringes 200 and the like is obtained from RFID chip 214 thereof by RFID reader 122 and stored in chemical liquid injector 100, and if a newly obtained production number is already stored, a check alarm is output.

Alternatively, it is possible that a rewritable product is used as RFID chip 214 of liquid syringe 200, chemical liquid injector 100 records the "used" or the fact that liquid syringe 200 has been mounted and the liquid thereof has been injected on RFID chip 214 thereof, and a check alarm is output when the data "used" is obtained from RFID chip 214 of newly mounted liquid syringe 200.

Since a large number of production numbers do not need to be stored in chemical liquid injector 100 in this case, an overflow or the like of RAM 133 can be prevented, and RAM 133 having a large capacity does not need to be included uselessly. In addition, even when the data stored in chemical liquid injector 100 is reset erroneously, inappropriately repeated use of liquid syringe 200 or the like can be prevented.

In the above embodiment, the control data for the liquid injection is obtained from RFID chip 214 of liquid syringe 200 and the like into chemical liquid injector 100, and chemical liquid injector 100 controls the operation of the liquid injection based on the control data. It is also possible to control the operation of the liquid injection based on a combination of control data obtained from RFID chip 214 of liquid syringe 200 and the like by chemical liquid injector 100 and control data entered through touch panels 104 and 121 and operation panel 103.

For example, it is possible that the variable pattern of liquid injection over time is recorded on RFID chip 214 of liquid syringe 200 as described above, and when an operator enters the data of an area to be imaged by MRI apparatus 300 through touch panels 104 and 121, the variable pattern is adjusted in accordance with the area to be imaged.

In the above embodiment, chemical liquid injector 100 finishes the injection operation and registers the production number obtained from RFID chip 214 of liquid syringe 200, and then finishes the various types of operations. Alternatively, for example, it is possible that when chemical liquid injector 100 finishes the injection operation and registration of the production number as described above and detects removal of contrast medium/physiological saline syringes 200C and 200W with RFID reader 122, chemical liquid injector 100 moves associated contrast medium/physiological saline injection mechanisms 117C and 117W backward to the initial positions at the backend.

It is also possible that when chemical liquid injector 100 completes the various types of operations and moves contrast medium/physiological saline injection mechanisms 117C and 117W back to the home positions and then detects the mounting of new contrast medium/physiological saline syringes 200C and 200W with RFID reader 122, chemical liquid injector 100 automatically moves associated contrast medium/physiological saline injection mechanisms 117C and 117W forward to the standby positions for holding piston members 210. In this case, liquid syringe 200 can be removed and put in chemical liquid injector 100 in an appropriate timing to place liquid injection mechanism 117 automatically to the appropriate position, so that any special operation is not required to place liquid injection mechanism 117 and the convenience can be improved.

In the above embodiment, RFID chips 214 are placed on liquid syringe 200 and extension tube 230. However, RFID chip 214 may be put only on liquid syringe 200, or RFID chip 214 may be mounted on the various types of peripheral device for the syringe such as a catheter and a liquid bottle other than extension tube 230 (not shown).

In the above embodiment, RFID chips 214 are placed on liquid syringe 200 and extension tube 230. Alternatively, for example, RFID chip 214 having various types of data about a patient set thereon may be placed on a peripheral tool for a patient such as a wristband put on an arm of the patient and a medical chart on which various types of data about the patient are written (not shown).

In this case, since the various types of data of the patient can be easily entered into chemical liquid injector 100, the injection operation can be controlled in accordance with the weight and age of the patient, for example. It is also possible to automatically prevent injection of a liquid which is not effective in the disease of the patient.

In the above embodiment, the various types of data of liquid syringe 200 and the like are entered into chemical liquid injector 100 with RFID chip 214. In addition, for example, the data from RFID chip 214 can be used to update the computer program or the resources in chemical liquid injector 100.

In the above embodiment, chemical liquid injector 100 having contrast medium/physiological saline injection mechanisms 117C and 117W injects the contrast medium and physiological saline. It is also possible to realize a chemical liquid injector which injects only a contrast medium with one liquid injection mechanism 117 or a chemical liquid injector which injects three or more liquids with three or more liquid injection mechanisms 117 (not shown).

In the above embodiment, MRI apparatus 300 is used as the diagnostic imaging apparatus and chemical liquid injector 100 injects the contrast medium for MR. For example, a CT scanner or a PET apparatus may be used as the diagnostic imaging apparatus and the chemical liquid injector may inject a contrast medium therefor.

In the above embodiment, CPU 131 operates in accordance with the computer program stored in RAM 133 or the like to realize logically various means as various functions of chemical liquid injector 100. Each of the various means may be formed as specific hardware, or some of them may be stored as software on ROM 133, while others may be formed as hardware.

In the above embodiment, the various types of data are recorded by the manufacturer on RFID chip 214 of liquid syringe 200 or extension tube 230. Alternatively, the various types of data may be recorded on RFID chip 214 of liquid syringe 200 or the like in a medical facility such as a hospital where liquid syringe 200 is used.

In this case, desired data can be provided for liquid syringe 200 in the medial facility. Thus, when a desired liquid is filled into liquid syringe 200 of the refill type, various types of data of the liquid can be recorded on RFID chip 214. In such a case, however, it is preferable that the production number is previously recorded on RFID chip 214 to prevent repeated use of liquid syringe 200 as described above.

In the above embodiment, RFID reader 122 for obtaining the various types of data from RFID chip 214 of liquid syringe 200 is placed on chemical liquid injector 100. Alternatively, RFID reader 122 may be placed on a liquid warmer for keeping liquid syringe 200 at an appropriate temperature (not shown).

In this case, the liquid warmer can control the heat-retaining operation based on the various types of data obtained from RFID chip 214 to keep the liquid at the appropriate temperature. It is also possible that the liquid warmer transmits the data recorded on RFID chip 214 to the chemical liquid injector having no RFID reader 122.

What is claimed is:

1. A chemical liquid injection system including:
   a liquid syringe having a piston member being inserted slidably into a cylinder member filled with a contrast medium, and a chemical liquid injector having a liquid injection mechanism for relatively moving the cylinder member and the piston member of the liquid syringe exchangeably mounted on the chemical liquid injector to inject the liquid into a patient; wherein
   said liquid syringe further comprises an RFID (Radio Frequency Identification) chip having various types of data, including data on a resistance to pressure and data for checking conditions, recorded thereon, the RFID chip being mounted on said liquid syringe, and
   said chemical liquid injector further comprises:
   an RFID reader for obtaining the various types of data recorded on the RFID chip;
   an injection control unit having operation control means configured to perform a predetermined operation in accordance with at least some of the various types of obtained data and a first data display means configured to display various types of data;
   an injection head formed separately from the injection control unit, at least the liquid injection mechanism being mounted on the injection head; and
   a second data display means configured to display various types of data, wherein the second display means is disposed at a position away from the injection control unit, wherein
   the operation control means comprises a data holding means configured to hold the data including the data on the resistance to pressure from said RFID chip, an injection control means configure to control the operation of the liquid injection mechanism in accordance with the data on the resistance to pressure held in the data holding means, a data storing means configured to store predetermined check conditions as data and a data collating means configured to collate the stored check conditions with the data for checking conditions obtained from said RFID chip so that a check alarm can be output based on the collation result, the second data display means is a touch panel which also receives an entry operation, and the chemical liquid injection system is configured to display at least some of the various types of data obtained from said RFID chip at least on the second display means, and to allow an operator adjusting the operation based on the data obtained from the RFID chip by using the touch panel.

2. The chemical liquid injection system according to claim 1, wherein said operation control means comprises a display control means configured to cause at least the second data display means to output at least some of the various types of held data.

3. The chemical liquid injection system according to claim 1 wherein said RFID reader is mounted on the injection head.

4. The chemical liquid injection system according to claim 1, wherein said RFID reader is placed at a position where the RFID reader detects said RFID chip of the mounted liquid syringe in said chemical liquid injector.

5. The chemical liquid injection system according to claim 4, wherein said operation control means controls the liquid injection mechanism to enable its operation only when said RFID reader detects said RFID chip.

6. The chemical liquid injection system according to claim 4, wherein said operation control means places the liquid injection mechanism at an initial position when the completion of injection operation is detected and then the detection of said RFID chip by said RFID reader is finished.

7. The chemical liquid injection system according to claim 1, wherein said liquid syringe is of a pre-filled type which is shipped with the contrast medium filled thereinto, said RFID chip of the liquid syringe has a variable pattern set thereon for changing an injection rate of the contrast medium with time, and said operation control means changes the operation rate of the liquid injection mechanism with time in accordance with the variable pattern.

8. The chemical liquid injection system according to claim 1, wherein said RFID chip has at least a production number of each of said liquid syringes set thereon, said operation control means further comprises data accumulating means for storing the production number of said liquid syringe which was mounted and used to perform injection operation and an alarm outputting means configured to output the check alarm, said data collating means collates the stored production number with the production number of a newly mounted liquid syringe, and said alarm outputting means causes at least the second data display means to output the check alarm when the collated production numbers match.

9. The chemical liquid injection system according claim 1, wherein said liquid syringe has said RFID chip mounted thereon, the fact that the liquid syringe is used once or "used" being recorded as data on said RFID chip, said operation control means further comprises an alarm outputting means configured to output the check alarm, said operation control means further comprises data recording means for recording the "used" on said RFID chip of the liquid syringe which was mounted and used to perform injection operation, and said alarm outputting means cause at least the second data display means to output the check alarm when the "used" is obtained from said RFID chip of the liquid syringe.

10. The chemical liquid injection system according to claim 1, further comprising peripheral device for the syringe including a hollow needle-like member inserted into the patient to flow the liquid, an extension tube connecting the needle-like member to said liquid syringe to flow the liquid, and a unidirectional valve inserted into the extension tube to regulate the flow direction of the liquid, and an RFID chip having various types of data recorded thereon being mounted on each peripheral device for the syringe.

11. The chemical liquid injection system according to claim 1, further comprising peripheral tool for the patient including a wristband put on an arm of the patient and a medical chart on which various types of data about the patient are written, and an RFID chip having various types of data about the patient recorded thereon being mounted on each peripheral tool for the patient.

12. The chemical liquid injection system according to claim 1, further comprising a liquid warmer for keeping the liquid in the mounted liquid syringe at an appropriate temperature with a heat-retaining mechanism, the liquid warmer being provided separately from said chemical liquid injector, wherein the liquid warmer comprises:

an RFID reader for obtaining the various types of data recorded on said RFID chip; and an operation control means for performing a predetermined operation in accordance with at least some of the various types of obtained data.

13. A chemical liquid injector in the chemical liquid injection system according to claim 1, comprising:

an RFID reader for obtaining the various types of data, including data on a resistance to pressure and data for checking conditions, recorded on the RFID chip; and an injection control unit having an operation control means configured to perform a predetermined operation in accordance with at least some of the various types of obtained data and a first data display means configured to display various types of data, an injection head formed separately from the injection control unit, at least the liquid injection mechanism being mounted on the injection head, and a second data display means configured to display various types of data, wherein the second display means disposed at a position away from the injection control unit, wherein the operation control means comprises a data holding means configured to hold the various types of the data including the data for the operation of the liquid injection mechanism obtained from the RFID chip, an injection control means configure to control the operation of the liquid injection mechanism in accordance with the data for the operation of the liquid injection mechanism held in the data holding means, a data storing means configured to store predetermined check conditions as data and a data collating means configured to collate the stored check conditions with the data for checking conditions obtained from the RFID chip so that a check alarm can be output based on the collation result, the second data display means is a touch panel which also receives an entry operation, and the chemical liquid injector is configured to display at least some of the various types of data obtained from said RFID chip at least on the second display means, and to allow an operator adjusting the operation based on the data obtained from the RFID chip by using the touch panel.

14. A liquid warmer in the chemical liquid injection system according to claim 12, comprising:

an RFID reader for obtaining the various types of data recorded on the RFID chip; and an operation control means for performing a predetermined operation in accordance with at least some of the various types of obtained data.

15. The chemical liquid injection system according to claim 1, said chemical liquid injector automatically moves the liquid injection mechanism forward to a position for holding the piston member when the chemical liquid injector detects the mounting of the liquid syringe by detecting the RFID chip with the RFID reader.

16. The chemical liquid injection system according to claim 1, wherein the various types of data include expiration data of a liquid filled in said liquid syringe, said operation control means further comprises an alarm outputting means configured to output the check alarm, said data storing means stores the current date and time as the check conditions, said data collating means collates the stored current date and time with the expiration data obtained from the RFID chip, and said alarm outputting means causes at least the second data display means to output the check alarm when the current date and time is after the expiration date.

17. The chemical liquid injection system according to claim 1, further comprising other medical device connected to the chemical liquid injector through a communication network, and wherein the chemical liquid injector transmits information detected by the chemical liquid injector to the other medical device and the other medical device uses the information for operation of the other medical device.

18. The chemical liquid injection system according to claim 17, wherein the information transmitted from the chemical liquid injector to the other medical device is information which is detected trough a communication between the RFID chip and the RFID reader.

19. The chemical liquid injection system according to claim 17, wherein the other medical device is a diagnostic imaging apparatus.

* * * * *

UNITED STATES PATENT AND TRADEMARK OFFICE
CERTIFICATE OF CORRECTION

| | | |
|---|---|---|
| PATENT NO. | : 9,028,446 B2 | |
| APPLICATION NO. | : 13/169497 | |
| DATED | : May 12, 2015 | |
| INVENTOR(S) | : Shigeru Nemoto and Nobuhisa Tano | |

It is certified that error appears in the above-identified patent and that said Letters Patent is hereby corrected as shown below:

On the title page, (item 57 – abstract), line 6, "For, example," should be --For example,--.

In the specification,
Col. 1, line 12, "there" should be --their--.
Col. 1, line 45, "wholley" should be --wholly--.
Col. 3, line 42, "means" should be --means.--.
Col. 6, line 25, "s117" should be --117--.
Col. 6, line 57, "6A1" should be --6Al--.
Col. 8, line 41, "of" should be --of;--.
Col. 11, line 25, after "apparatus" insert --300--.

In the claims,
Col. 17, line 62 (claim 9), after "according" insert --to--.
Col. 19, line 24 (claim 16), "data" should be --date--.
Col. 20, line 4 (claim 16), "data" should be --date--.

Signed and Sealed this
Twelfth Day of April, 2016

Michelle K. Lee
*Director of the United States Patent and Trademark Office*